(12) United States Patent
Takahashi

(10) Patent No.: US 8,976,928 B2
(45) Date of Patent: Mar. 10, 2015

(54) RADIOGRAPHIC APPARATUS AND IMAGE ACQUIRING METHOD

(75) Inventor: Wataru Takahashi, Uji (JP)

(73) Assignee: Shimadzu Corporation, Kyoto (JP)

(*) Notice: Subject to any disclaimer, the term of this patent is extended or adjusted under 35 U.S.C. 154(b) by 478 days.

(21) Appl. No.: 13/392,389

(22) PCT Filed: Sep. 2, 2009

(86) PCT No.: PCT/JP2009/004322
§ 371 (c)(1),
(2), (4) Date: Feb. 24, 2012

(87) PCT Pub. No.: WO2011/027390
PCT Pub. Date: Mar. 10, 2011

(65) Prior Publication Data
US 2012/0148017 A1     Jun. 14, 2012

(51) Int. Cl.
*G01N 23/04* (2006.01)
*G01N 23/06* (2006.01)
(Continued)

(52) U.S. Cl.
CPC ............ *A61B 6/4035* (2013.01); *A61B 6/032* (2013.01); *A61B 6/485* (2013.01); *A61B 6/542* (2013.01); *G21K 1/10* (2013.01)
USPC .................. 378/62; 378/86; 378/87; 378/90; 378/156

(58) Field of Classification Search
CPC ....... G01N 23/08; G01N 23/083; G21K 1/00; G21K 3/00; G06K 9/20; G06K 9/40; G06K 9/60; G02B 5/22; H05G 1/60; H05G 1/64
USPC .......... 378/4–20, 56, 62, 91, 98, 98.8, 98.12, 378/156, 158, 207, 210, 901, 86, 87; 382/128, 131, 274, 885, 888, 889, 892
See application file for complete search history.

(56) References Cited

U.S. PATENT DOCUMENTS 5,568,533 A    10/1996   Kumazaki et al.
5,666,391 A *   9/1997   Ohnesorge et al. ............... 378/7
(Continued)

FOREIGN PATENT DOCUMENTS

JP      7-184885 A     7/1995
JP      7-255712 A    10/1995
(Continued)

*Primary Examiner* — Anastasia Midkiff
(74) *Attorney, Agent, or Firm* — McDermott Will & Emery LLP

(57) ABSTRACT

This invention has one object to provide radiographic apparatus with a compensating filter that allows simple and accurate estimation of direct radiation to acquire a radioscopic image or a sectional image of excellent contrast. This invention includes a direct-ray attenuation-rate acquiring section for acquiring a direct-ray attenuation rate from a dose of direct radiation entering into a subject and a dose of direct radiation emitted from the subject. In this invention, a direct-ray attenuation rate is acquired on an assumption that a primary indirect-ray attenuation rate is equal to the direct-ray attenuation rate, the primary indirect-ray attenuation rate being a rate of decreasing a primary indirect-ray generated with the compensating filter that transmits the subject. Such configuration may achieve provision of X-ray apparatus that allows more simple acquisition of a fluoroscopic X-ray image or a sectional image without performing complicated calculations conventionally.

7 Claims, 9 Drawing Sheets

(51) Int. Cl.
*G01N 23/20* (2006.01)
*A61B 6/00* (2006.01)
*A61B 6/03* (2006.01)
*G21K 1/10* (2006.01)

(56) References Cited

U.S. PATENT DOCUMENTS

| | | | | |
|---|---|---|---|---|
| 5,771,269 | A | * | 6/1998 | Chao ................................. 378/5 |
| 5,878,108 | A | * | 3/1999 | Baba et al. .................... 378/98.4 |
| 8,326,011 | B2 | * | 12/2012 | Star-Lack et al. ............. 382/131 |
| 2004/0008810 | A1 | * | 1/2004 | Nelson et al. .................... 378/19 |
| 2006/0008046 | A1 | * | 1/2006 | Ruhrnschopf .................... 378/7 |
| 2007/0189444 | A1 | * | 8/2007 | Van Steven-Daal et al. ..... 378/6 |
| 2008/0013673 | A1 | | 1/2008 | Ruhmschopf |
| 2010/0239145 | A1 | * | 9/2010 | Fujita ............................ 382/131 |
| 2010/0272236 | A1 | * | 10/2010 | Hirooka et al. ................. 378/62 |

FOREIGN PATENT DOCUMENTS

| | | |
|---|---|---|
| JP | 2000-107163 A | 4/2000 |
| JP | 2008-502395 A | 1/2008 |

* cited by examiner

Fig.5
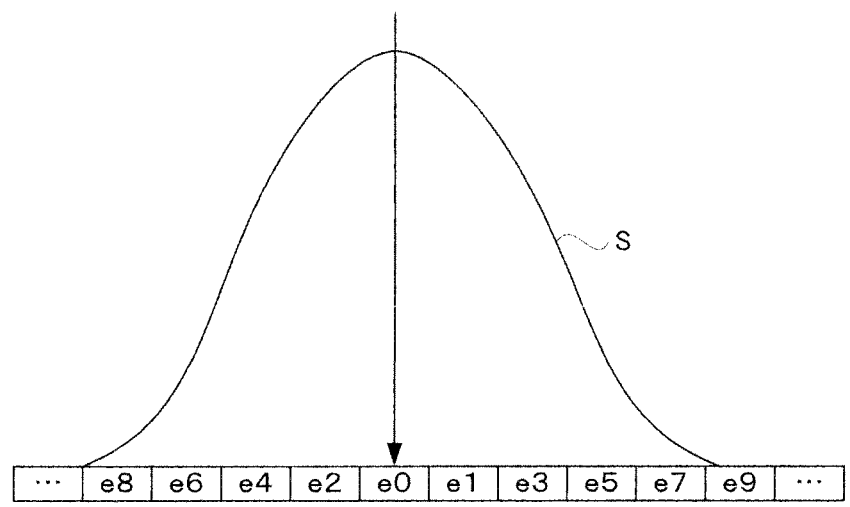
Fig.6
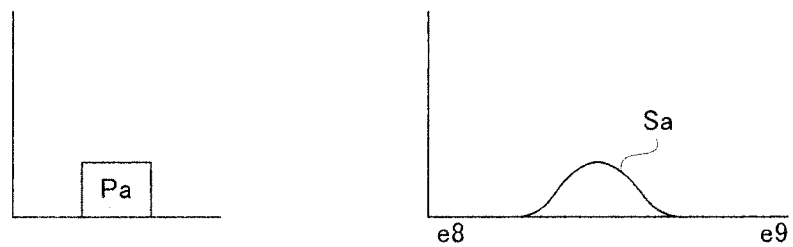
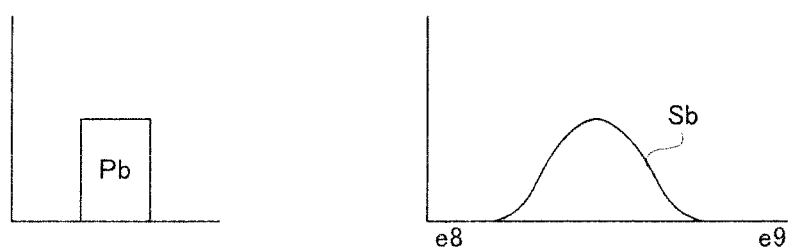
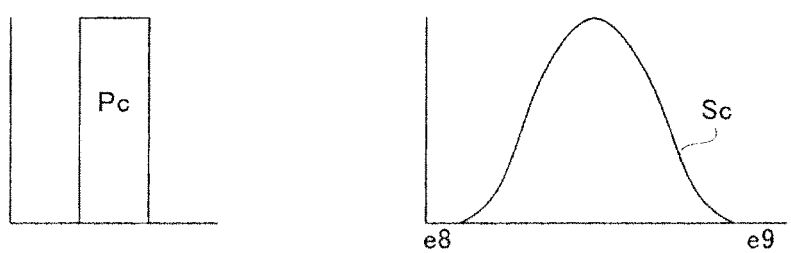

Fig.7
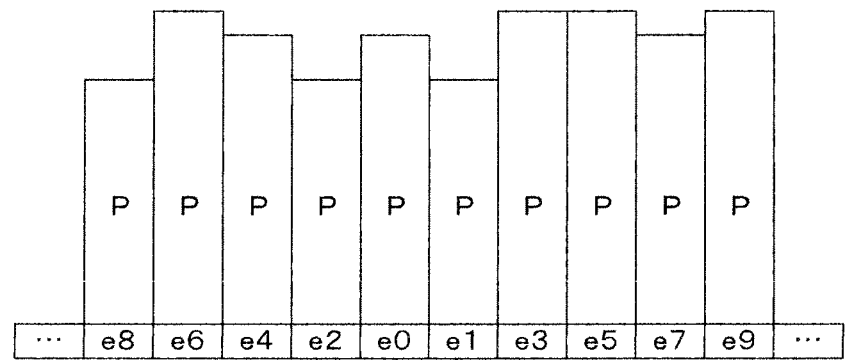
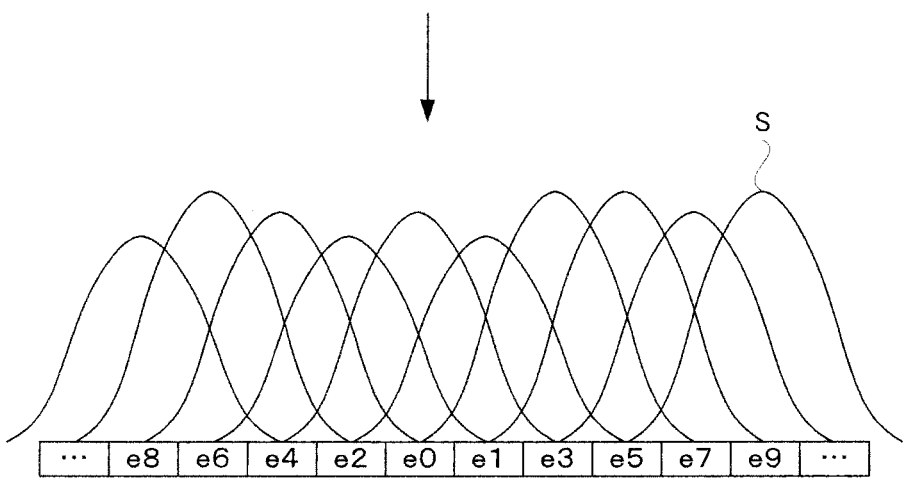
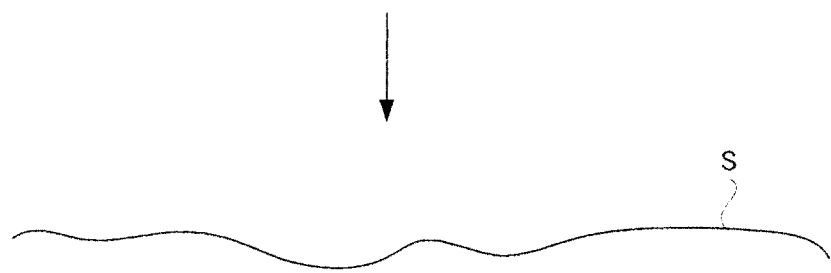
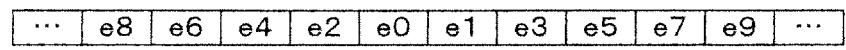

RADIOGRAPHIC APPARATUS AND IMAGE ACQUIRING METHOD

CROSS REFERENCE TO RELATED APPLICATIONS

This application is a U.S. National Stage application under 35 U.S.C. §371, of International Application PCT/JP2009/004322 filed on Sep. 2, 2009, which was published as WO 2011/027390 A1 on Mar. 10, 2011. The application is incorporated herein by reference.

TECHNICAL FIELD

This invention relates to radiographic apparatus and a method for acquiring a fluoroscopic imaging of a subject through irradiating with radiation. More particularly, this invention relates to radiographic apparatus with a compensating filter and a method of acquiring an image, the compensating filter producing variations in intensity of radiation to be emitted to the subject.

BACKGROUND

Medical institutions are equipped with radiographic apparatus for acquiring a fluoroscopic image of a subject. Now, description will be given of a construction of a conventional radiographic apparatus. As shown in FIG. 12A, conventional radiographic apparatus 51 includes a top board 52 for supporting a subject M, a radiation source 53 for emitting radiation, and a radiation detector 54 for detecting radiation.

Radiation is emitted from the radiation source 53, and then radiation beams B transmit the subject M to enter into the detector 54. The detection signals outputted from the detector 54 are constructed into a fluoroscopic image.

Here, the radiation source 53 emits a uniform dose of radiation trough the radiation beams B. Accordingly, when an image is acquired under a state where the subject M is not placed on the top board 52, the pixel values are approximately uniform throughout the image. On the other hand, when a fluoroscopic image of the subject M is generated under the above state, a radiation fluoroscopic image P to be acquired has an insufficient dose of radiation at a center thereof. As a result, the image has a dark portion at the center of the subject M. See FIG. 12B. The reason therefor is as under. That is, the subject M has a largest thickness at a center thereof in a body axis direction. The thickness gradually decreases from the center toward the periphery. Accordingly, it is more difficult for the radiation beams B to transmit through the center of the subject M rather than the periphery.

The radiation source 53 is provided with a compensating filter 55 for avoiding such partial exposure variations to the detector 54. The radiation beams B transmitting through the compensating filter 55 have a high dose of radiation at a center c in the body axis direction than a periphery portion s. See U.S. Pat. No. 5,666,391.

The conventional configuration, however, has the following problem. That is, when radiation transmits the compensating filter 55, scattered radiation in modified traveling directions is generated, which leads to reduced visibility of the radioscopic image. The radiation emitted from the radiation source 53 transmits the compensating filter 55 toward the detector 54. Herein, radiation is to be generated having traveling directions modified due to collision with electrons that form the compensating filter 55. Such radiation is called scattered radiation (which may also be referred to as primary scattered radiation), and may lead to a lower-contrast radioscopy image. Especially, such problem will notably occur in cone-beam imaging where more scattered radiation is generated.

Such scattered radiation (which may also be referred to as secondary scattered radiation) is also generated when radiation beams B transmit the subject M. There is a conventional configuration of acquiring a radioscopic image as under. Specifically, an estimate calculation is performed on the assumption that radiation detected by the detector 54 is the sum of direct radiation (i.e., radiation that has reached the detector 54 without being scattered) and scattered radiation, whereby direct-radiation intensity is calculated. Based on this, a radioscopic image is to be acquired. A radioscopic image of excellent contrast may be acquired with only direct radiation.

Here, scattered radiation generated through the compensating filter 55 becomes obstructive in such estimation of direct-radiation intensity. In other words, the foregoing estimating method is performed on the assumption that scattered radiation is generated by the subject M. Accordingly, merely application of the conventional estimating method to the configuration where scattered radiation is generated at two parts of the compensating filter 55 and the subject M cannot achieve accurate estimation of direct radiation.

Then, methods of removing influence of scattered radiation to the compensating filter 55 include an approach of determining in advance direct radiation having transmitted the compensating filter 55. Specifically, in estimation of direct radiation, a slit S as in FIG. 13 is used for emitting only direct radiation toward each one detecting element e that forms the detector 54 to determine intensity of the direct radiation. According to this method, direct radiation to every detecting element e is successively determined while the slit S moves. This is very laborious. Moreover, the slit S need to move precisely. In addition, when the compensating filter 55 is replaced in accordance with imaging, the energy of X-rays emitted from the radiation source 53 is changed, or a distance varies between the radiation source 53 and the detector 54, scattering of radiation from the compensating filter 5 varies accordingly. As a result, direct radiation has to be determined with use of the slit S for every variation in imaging condition. Therefore, the method using the slit S is not considered as an actual solution.

In the conventional estimating method, radiation detected by the detector 54 may be separated into scattered radiation scattered through an object and direct radiation not scattered. Accordingly, a method may be considered that direct radiation is estimated in advance through execution of imaging under a state where the subject M is not placed on the top board 52 (i.e., air radiography). Specifically, direct radiation is estimated that transmits the compensating filter 55 in air radiography. Thereafter, radiography is again performed with the subject M placed on the top board 52. Accordingly, direct radiation may be estimated that transmits the subject M. On the other hand, this method needs two steps of calculations, i.e., determination of direct radiation transmitting the compensating filter 55 and determination of an amount of the radiation scattered through the subject M. Thus, time is involved until the end of the calculations. That is, estimate calculation of scattered radiation is performed in air radiography, and thereafter estimate calculation of scattered radiation is performed with the subject M being placed on the top board 52. Accordingly, time and labor will be spent the calculations.

This invention has been made regarding the state of the art noted above, and its object is to provide radiographic apparatus with a compensating filter that allows simple and accurate estimation of direct radiation to acquire a radioscopic image or a sectional image with excellent contrast.

SUMMARY

Radiographic apparatus according to examples of the invention include a radiation source, a compensating filter, a detecting device, (A) an air-data storage device, (B) a subject-data storage device, (C) a secondary scattered-ray estimating device, (D) a direct-ray attenuation-rate acquiring device, and (E) an image generating device. The radiation source emits radiation. The compensating filter is provided on the radiation source and controls a dose of radiation. The detecting device detects radiation transmitting the compensating filter to output detection data. The air-data storage device stores air data as detection data that is acquired with a subject not placed between the radiation source and the detecting device. The subject-data storage device stores subject data as detection data that is acquired with the subject placed between the radiation source and the detecting device. The secondary scattered-ray estimating device estimates a dose of secondary scattered radiation that enters into the detecting device based on the subject data, the secondary scattered radiation being as scattered radiation generated with the subject. The direct-ray attenuation-rate acquiring device acquires a direct-ray attenuation rate based on the air data, the subject data, and an estimated dose of the secondary scattered radiation, the direct-ray attenuation rate being as a rate of decreasing direct radiation emitted from the compensating filter through transmitting the subject. The image generating device generates an image having a subject image appearing therein in accordance with the direct-ray attenuation rate. The direct-ray attenuation-rate acquiring device acquires a direct-ray attenuation rate on an assumption that a primary scattered-ray attenuation rate is equal to the direct-ray attenuation rate, the primary scattered-ray attenuation rate representing a rate of decreasing a primary scattered-ray that transmits the subject, the primary scattered ray being as scattered radiation generated with the compensating filter.

Examples of the invention include the direct-ray attenuation-rate acquiring device for acquiring a direct-ray attenuation rate from a dose of direct radiation entering into the subject and a dose of direct radiation emitted from the subject. Determination of the direct-ray attenuation rate may achieve acquisition of a radiographic image or a sectional image of an excellent contrast with no influence of scattered radiation. On the other hand, the radiographic apparatus according to this invention includes the compensating filter for controlling a dose of radiation that has some difficulty in acquiring the direct-ray attenuation rate. This invention solves this difficulty as follows.

Primary scattered-radiation generated through the compensating filter attenuates in the subject and enters into the detecting device. The way of determining the attenuated primary scattered-radiation becomes important upon acquisition of a direct-ray attenuation rate. In this invention, a direct-ray attenuation rate is acquired on an assumption that a primary scattered-ray attenuation rate is equal to the direct-ray attenuation rate, the primary scattered-ray attenuation rate being as a rate of decreasing scattered radiation that passes through (transmits) the subject. Here, primary scattered-radiation is radiation with a traveling direction and energy thereof being slightly changed due to Compton scattering. In other words, the behavior of attenuating the primary scattered-radiation in the subject may be considered similar to that of attenuating direct radiation. As noted above, it is assumed that the primary scattered-ray attenuation rate is equal to the direct-ray attenuation rate. Accordingly, an amount of direct radiation transmitting through the subject may be determined without performing complicated calculations conventionally. Therefore, radiographic apparatus may be provided that allows more simple acquisition of a radiographic image or a sectional image.

Moreover, the foregoing direct-ray attenuation-rate acquiring device preferably acquires a direct-ray attenuation rate as under. That is, a value of subtracting the estimated secondary scattered-radiation intensity from radiation intensity determined from the subject data is divided by radiation intensity determined from the air data.

The above configuration describes a specific calculation manner by the direct-ray attenuation-rate acquiring device. The direct-rays attenuation rate may be acquired through the simple calculation as above.

Moreover, the compensating filter is preferably removable from the radiation source.

Moreover, the compensating filter may include, instead of the foregoing configuration, a plurality of parts variable in relative position therebetween. The compensating filter may further include a compensating filter moving device for moving the parts, and a compensating filter control device for controlling the compensating filter moving device.

With the foregoing configuration, the compensating filter may be modified optionally according to purposes of imaging. In addition, even when the compensating filer is replaced or changed in shape, once performance of air radiography may achieve accurate acquisition of the direct-ray attenuation rate.

Moreover, a supporting portion, a rotating device, and a rotation control device are included. The supporting portion supports the radiation source and the detecting device. The rotating device rotates the supporting portion. The rotation control device controls the rotating device. The image generating device generates a sectional image in accordance with a series of direct-ray attenuation rates acquired while the supporting portion is rotated. Such configuration is desirable.

The foregoing configuration allows acquisition of the sectional image of the subject. Specifically, the foregoing configuration achieves acquisition of a series of direct-ray attenuation rates while the supporting portion is rotated. Moreover, the image generating device generates a sectional image based on a series of the direct-ray attenuation rates. Accordingly, radiographic apparatus may be provided that allows acquisition of an excellent-contrast sectional image.

Moreover, this invention discloses a method of obtaining an image with use of detection data acquired by radiographic apparatus including a radiation source, a compensating filter, and a detecting device. The radiation source emits radiation. The compensating filter is provided on the radiation source and controls a dose of radiation. The detecting device detects radiation transmitting the compensating filter to output detection data. The method includes (a) an air-data acquiring step, (b) a subject-data acquiring step, (c) a secondary scattered-ray estimating step, (d) a direct-ray attenuation-rate acquiring step, and (e) an image generating step. The air-data acquiring step is performed for acquiring air data as detection data that is acquired with a subject not placed between the radiation source and the detecting device. The subject-data acquiring step is performed for acquiring subject data as detection data that is acquired with the subject placed between the radiation source and the detecting device. The secondary scattered-ray estimating step is performed for estimating a dose of secondary scattered radiation that enters into the detecting device based on the subject data, the secondary scattered radiation being as scattered radiation generated with the subject. The direct-ray attenuation-rate acquiring step is performed for acquiring a direct-ray attenuation rate based on the air data, the subject data, and an estimated dose of the secondary scattered radiation, the direct-ray attenuation rate being as a rate of decreasing direct radiation emitted from the compensating filter through transmitting the subject. The image generating step is performed for generating an image having a subject image appearing therein in accordance with the direct-ray attenuation rate. In the direct-ray attenuation-rate acquiring step, a direct-ray attenuation rate being acquired on an assumption that a primary scattered-ray attenuation rate is equal to the direct-ray attenuation rate, the primary scattered-ray attenuation rate representing a rate of decreasing a primary scattered-ray that transmits the subject, the primary scattered ray being as scattered radiation generated with the compensating filter.

Examples of the invention include the direct-ray attenuation-rate acquiring step for acquiring a direct-ray attenuation rate from a dose of direct radiation entering into the subject and a dose of direct radiation emitted from the subject. Determination of the direct-ray attenuation rate may achieve acquisition of a radiographic image or a sectional image of excellent contrast with no influence of scattered radiation. On the other hand, the method of obtaining an image according to examples of the invention include the compensating filter for controlling a dose of radiation that has some difficulty in acquiring the direct-ray attenuation rate. Then, in the examples, the behavior of attenuating the primary scattered-radiation in the subject as a rate of decreasing the primary scattered-radiation that passes through the subject is considered similar to that of attenuating direct radiation for assumption that the primary scattered-ray attenuation rate is equal to the direct-ray attenuation rate. Based on this assumption, the direct-ray attenuation rate may be acquired. Such configuration may achieve an amount of direct rays transmitting the subject without performing complicated calculations conventionally. Therefore, the method of obtaining an image may be provided that allows more simple acquisition of a radiographic image or a sectional image.

Moreover, in the foregoing direct-ray attenuation-rate acquiring step, a direct-ray attenuation rate is preferably acquired by dividing a value of subtracting the estimated secondary scattered-radiation intensity from radiation intensity determined from the subject data, by radiation intensity determined from the air data.

The above configuration describes a specific calculation manner in the direct-ray attenuation-rate acquiring step. The direct-rays attenuation rate may be acquired through the simple calculation as above.

The examples of the invention include the direct-ray attenuation-rate acquiring device for acquiring a direct-ray attenuation rate from a dose of direct radiation entering into the subject and a dose of direct radiation emitted from the subject. Determination of the direct-ray attenuation rate may achieve acquisition of a radiographic image or a sectional image having an excellent contrast with no influence of scattered radiation. On the other hand, the method of obtaining an image according to the examples of the invention include the compensating filter for controlling a dose of radiation that has some difficulty in acquiring the direct-ray attenuation rate. Then, in the examples, the behavior of attenuating the primary scattered-radiation in the subject as a rate of decreasing the primary scattered-radiation that passes through the subject is considered similar to that of attenuating direct radiation for assumption that the primary scattered-ray attenuation rate is equal to the direct-ray attenuation rate. Based on this assumption, the direct-ray attenuation rate may be acquired. Such configuration may achieve an amount of direct rays transmitting the subject without performing complicated calculations conventionally. Therefore, radiographic apparatus may be provided that allows more simple acquisition of a radiographic image or a sectional image.

BRIEF DESCRIPTION OF THE DRAWINGS

FIGS. 5 to 9 are schematic views each showing a secondary scattered-ray estimating section according to the example.

DETAILED DESCRIPTION

Description is given hereafter for examples for implementing this invention. X-rays to be described hereunder correspond to the radiation in this invention.

Figure 1:
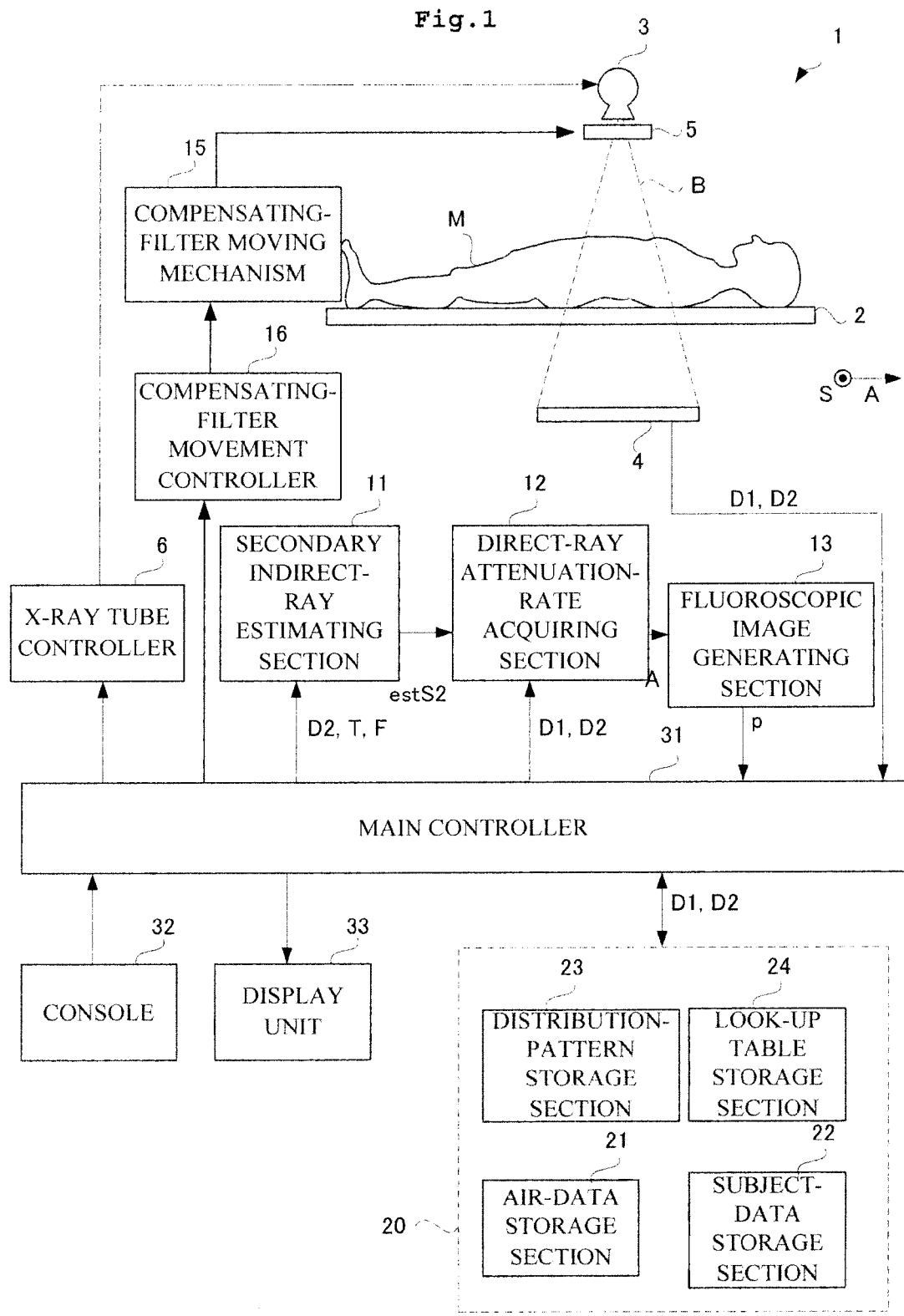
FIG. 1 is a functional block diagram showing X-ray apparatus according to an example.

Description will be given of a configuration of X-ray apparatus 1 according to an example. As shown in FIG. 1, the X-ray apparatus 1 according to this example includes a top board 2 for supporting a subject NI, an X-ray tube 3 provided above the top board 2 for emitting X-ray beams B toward the top board 2, a flat panel detector (FPD) 4 provided below the top board 2 for detecting X-rays, and an X-ray tube controller 6 for controlling the X-ray tube 3. The X-ray tube corresponds to the radiation source in this example. The FPD corresponds to the detecting device in this invention.

The FPD 4 has detecting elements for detecting X-rays that are arranged in a two-dimensional matrix to form an incidence surface where X-rays enter. The detecting elements are arranged in a 1,024 by 1,024 matrix, for example.

Figure 2:
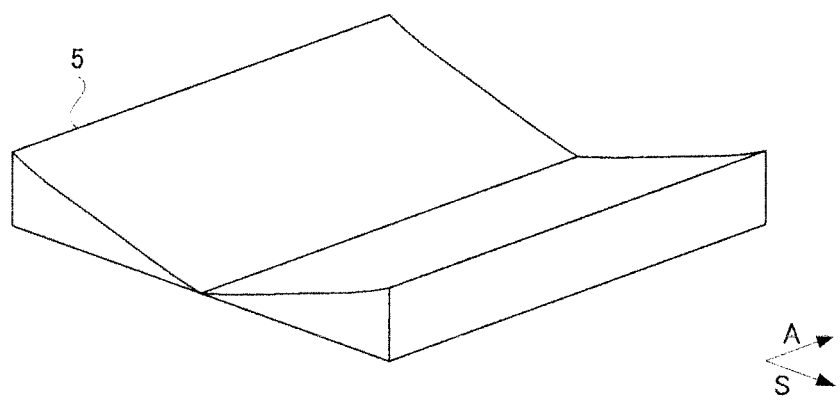
FIG. 2 is a perspective view showing a compensating filter according to the example.

The X-ray tube 3 includes a compensating filter 5 for providing given distributions of radiation intensity of X-ray beams B. Radiation emitted from the X-ray tube 3 transmits the compensating filter 5 toward the FPD 4. As shown in FIG. 2, the compensating filter 5 has thick portions larger in thickness in a direction where X-rays transmit. The thick portions are provided at both ends in an S-direction perpendicular to the body axis direction of the subject M and a direction from the X-ray tube 3 toward the FPD 4. The compensating filter 5 has a thickness decreasing from one thick portion toward the other thick portion, a region in the middle of the two thick portions being a thin portion of the smallest thickness. The compensating filter 5 absorbs more X-rays entering into the thick portion than into the thin portion. Here, X-ray beams B hereinafter refer to X-rays having transmitted through the compensating filter 5, except where specifically noted.

X-ray beams B emitted from the compensating filter 5 have partial dose deviations. That is, a dose of X-ray decreases toward both ends in the S-direction. When X-ray beams B as above transmit the subject M, a more dose of X-rays is absorbed in the middle of the subject M in the S-direction. That is because the subject M has a larger thickness in an X-ray irradiation direction. On the other hand, the subject M has a smaller thickness on both ends thereof in the S-direction, whereby a less dose of X-rays is absorbed. In other words, compensation is made of dose deviations X-ray beams B and absorption deviations of X-rays in the subject M, which results in elimination of partial deviations of X-ray intensity. Accordingly, X-rays are to enter into the FPD 4 uniformly.

The compensating filter 5 provided on the X-ray tube 3 is removable from the X-ray tube 3. The compensating filter 5 suitable for radiography may be selected to be attached to the X-ray tube 3.

Figure 3A:
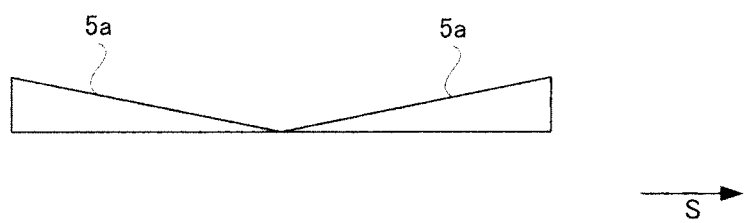
FIG. 3 is a schematic view showing the compensating filter according to the example.
Figure 3B:
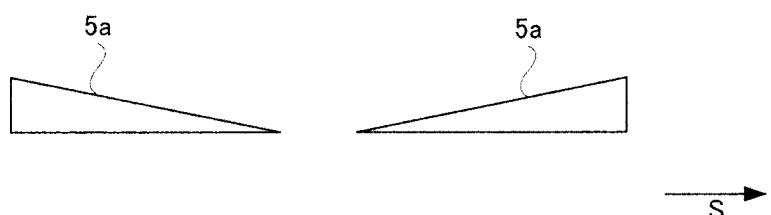
Figure 3C:
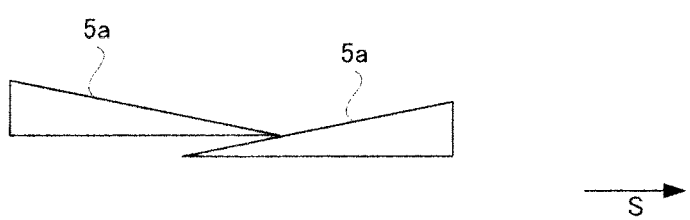
Figure 3D:
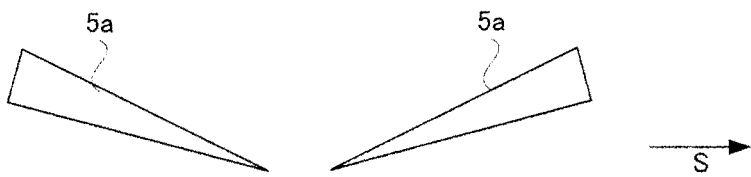
Figure 4:
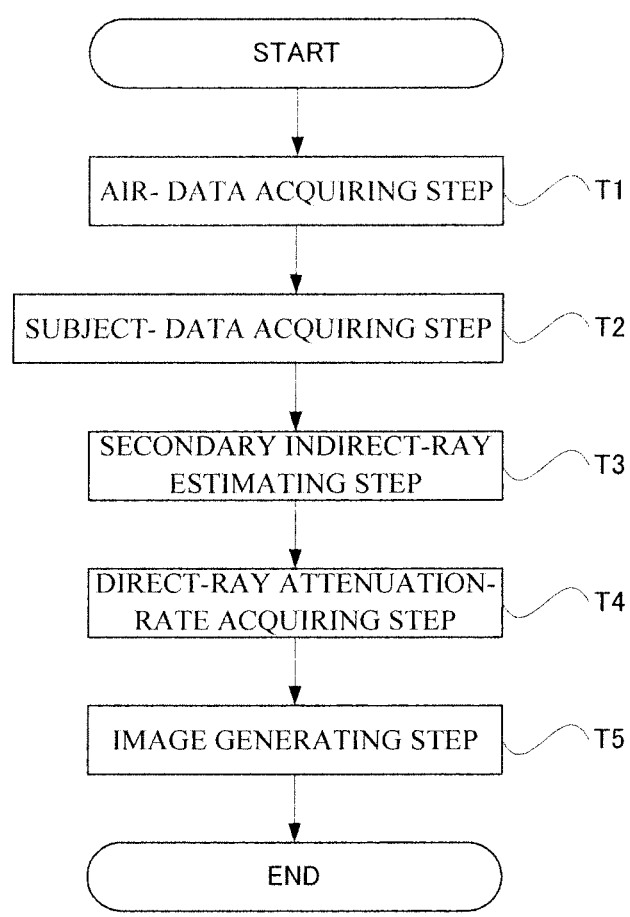
FIG. 4 is a flow chart showing operations of obtaining a fluoroscopic X-ray image according to the example.

Moreover, as shown in FIG. 1, the X-ray apparatus 1 according the example further includes a compensating-filter moving mechanism 15 for moving parts that forms the compensating filter 5 and a compensating-filter movement controller 16 for controlling the compensating-filter moving mechanism 15. The compensating filter 5 is divided into two parts 5a at the middle of thick portions, as shown in FIG. 3A. A relative position of the two parts 5a is variable. Specifically, as shown in FIG. 3B, the compensating filter moving mechanism 15 may move each part 5a in the S-direction to space away both parts 5a in the S-direction. Conversely, as shown in FIG. 3C, both parts 5a may be approached in the S-direction to overlap each other. Moreover, as shown in FIG. 3D, both parts 5a may be inclined such that the thin portions are moved away from the X-ray tube 3. The compensating-filter moving mechanism 15 corresponds to the compensating-filter moving device in this invention. The compensating-filter movement controller 16 corresponds to the compensating-filter movement control device in this invention.

The X-ray apparatus 1 also includes a data storage device 20 for storing each data. The data storage device 20 includes an air-data storage section 21, a subject-data storage section 22, a distribution-pattern storage section 23, and a look-up table storage section 24. The air-data storage section 21 stores air data D1. The subject-data storage section 22 stores subject data D2. The distribution-pattern storage section 23 stores distribution patterns F representing distributions of scattered X-rays. The look-up table storage section 24 stores look-up tables T correlated with the distribution patterns F and radiation intensity. The subject-data storage section corresponds to the subject-data storage device in this invention. The air-data storage section corresponds to the air-data storage section in this invention.

Moreover, the X-ray apparatus 1 includes a console 32 for inputting operator's instructions, and a display unit 33 for displaying a fluoroscopic X-ray image p. The X-ray apparatus 1 also includes a main controller 31 for performing an overall control of each section 6, 11, 12, 13, and 16. The main controller 31 has a CPU, and is achieved by executing various programs. The above sections each may be individually operated by arithmetic units that perform their functions.

Next, description is given hereinafter of operations of examples of the X-ray apparatus having such configuration. Operation of the X-ray apparatus 1 according to the example for acquiring a fluoroscopic X-ray image includes an air-data acquiring step T1, a subject-data acquiring step T2, a secondary scattered-ray estimating step T3, a direct-ray attenuation-rate acquiring step T4, and an image generating step T5. The air-data acquiring step T1 is performed for acquiring air data D1 through air radiography with the subject not placed between the X-ray tube 3 and the FPD 4. The subject-data acquiring step T2 is performed for acquiring subject data through subject radiography with the subject placed between X-ray tube 3 and the FPD 4. The secondary scattered-ray estimating step T3 is performed for estimating a dose of secondary scattered-radiation S2 that enters into the FPD 4 based on the subject data D2. The direct-ray attenuation-rate acquiring step T4 is performed for acquiring a direct-ray attenuation rate A based on the air data D1, the subject data D2, and the estimated secondary scattered-radiation S2. The image generating step T5 is performed for generating a fluoroscopic X-ray image having an image of the subject M appearing therein based on the direct-ray attenuation rate. Each of these steps will be described hereinafter in order.

Air-Data Acquiring Step T1

Firstly, X-ray is emitted under a state where the subject M is not placed on the top board 2. Here, the air-data storage section 21 stores detection data outputted from the FPD 4. The data stored in the air-data storage section 21 is the sum of direct radiation entering into the FPD 4 and scattered radiation. The scattered radiation herein is generated through the compensating filter 5. This is referred to as primary scattered X-rays S1. Where X-ray intensity represented by air-data D1 is Gair, the following relation exists:

$$Gair = P1 + S1 \quad (1)$$

P1 herein refers to direct radiation entering through the compensating filter 5 into the FPD 4 in air radiography. Unless otherwise radiographic conditions are modified, the previous air-data D1 may be adopted in air-data acquiring step T1. In this case, this step is to be skipped.

Subject-Data Acquiring Step T2

Subsequently, X-ray is emitted under a state where the subject M is placed on the top board 2. Here, the subject-data storage section 22 stores detection data outputted from the FPD 4. Here, X-ray intensity Gobj represented by the subject data D2 contains direct X-rays P2 having entered into the FPD 4 and secondary scattered X-rays S2 as scattered X-rays generated due to the subject. X-ray intensity Gobj also contains a portion of the primary scattered X-rays S1. The reason for containing a portion of the primary scattered X-rays S1 is that the primary scattered X-rays S1 generated through the compensating filter 5 enter and are absorbed into the subject, and thus a dose thereof decreases until they reaches the FPD 4. Therefore, the following relation is established:

$$Gobj = P2 + S2 + w(S1) \quad (2)$$

Here, w (S1) represents primary scattered X-rays S1 having a decreased dose due to transmitting the subject M.

Secondary Scattered-Ray Estimating Step T3

Then the subject data D2 is outputted to the secondary scattered-ray estimating section 1I where secondary scattered-rays S2 are estimated. Description will be given of operations of the secondary scattered-ray estimating section 11. As shown in FIG. 5, the FPD 4 has detecting elements of odd numbers e1 to e9 arranged in order from a detecting element e0 as a starting point on the right in plane of the figure (rearward side), and detecting elements of even numbers e2 to e8 arranged in order from the detecting element e0 as a starting point on the left in plane of the figure (forward side). When direct X-rays with given intensity are inputted into the detecting element e0, scattered radiation S appears within the detecting elements e0 to e9 with certain distributions, as shown in FIG. 5. The secondary scattered-ray estimating section corresponds to the secondary scattered-ray estimating device in this invention.

As shown in the right of FIG. 6, a distribution-pattern storage section 23 stores a plurality of distribution conditions on scattered radiation S, each of which corresponds to a distribution pattern F. For instance, it is assumed that three distribution patterns F are stored in the distribution-pattern storage device 23.

A look-up table storage section 24 stores look-up tables T, which are correlated with intensity of direct X-rays P detected by the detecting element e0 and distribution patterns Sa to Sc. Specifically, when direct X-rays P has intensity represented by Pa, Pb, Pc shown in the left of FIG. 6, scattered X-rays have corresponding distribution patterns F of Sa, Sb, Sc, respectively. It is assumed that direct X-ray intensity of the detecting element e0 in FIG. 5 corresponds to Pc in FIG. 6, scattered X-ray has a distribution pattern F of Sc.

Moreover, it is assumed that direct X-rays P are determined for the detecting elements e0 to e9 as upper side of FIG. 7. Accordingly, scattered-radiation intensity may be estimated. That is, scattered X-rays S are present with distributions for every detecting element e0 to e9. As shown in the middle of FIG. 7, distribution patterns F are distributed toward adjacent detecting elements. Consequently, the distribution patterns F overlap each other across the detecting elements. Accordingly, intensity of scattered X-rays in the detecting element e0 is determined by adding the distribution patterns F of scattered X-rays in the detecting elements e0 to e9. Thus, scattered X-ray intensity in each detecting element e0 to e9 is determined as in the lower side of FIG. 7.

As is seen from the foregoing description, it is necessary to determine direct X-rays P for each detecting element e0 to e9 in order to obtain scattered-radiation intensity. Instead of the direct X-rays P, subject data D2 with direct X-rays and scattered X-rays being summed up may be adopted. With such being the case, the secondary scattered-ray estimating section 11 performs the following operations. Specifically, the secondary scattered-ray estimating section 1 refers to X-ray intensity for every the detecting element in the subject data D2, and identifies a distribution pattern F of scattered X-rays corresponding to this based on the look-up table T. Then the secondary scattered-ray estimating section 11 reads out the distribution patterns F for each detecting element from the distribution-pattern storage section 23, and sums them up, thereby determining an estimate estS2 of secondary scattered X-rays.

Figure 8:
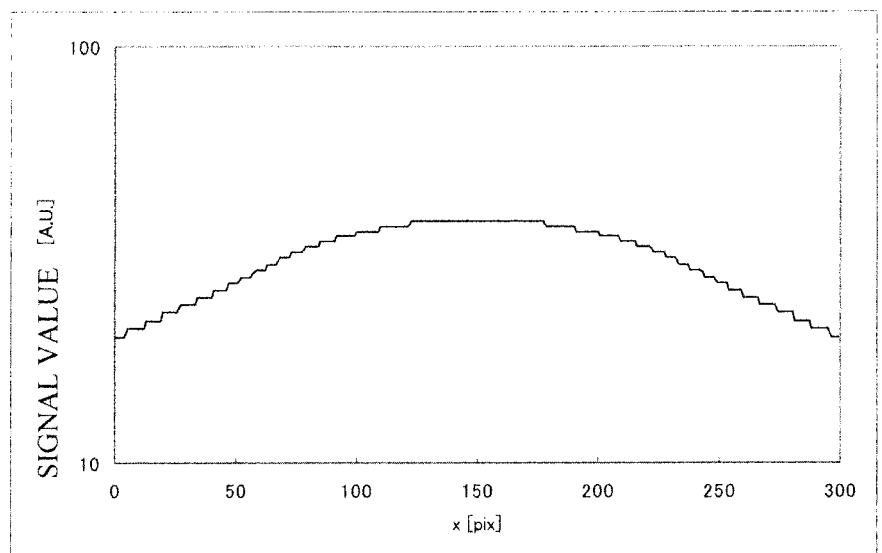
Figure 9:
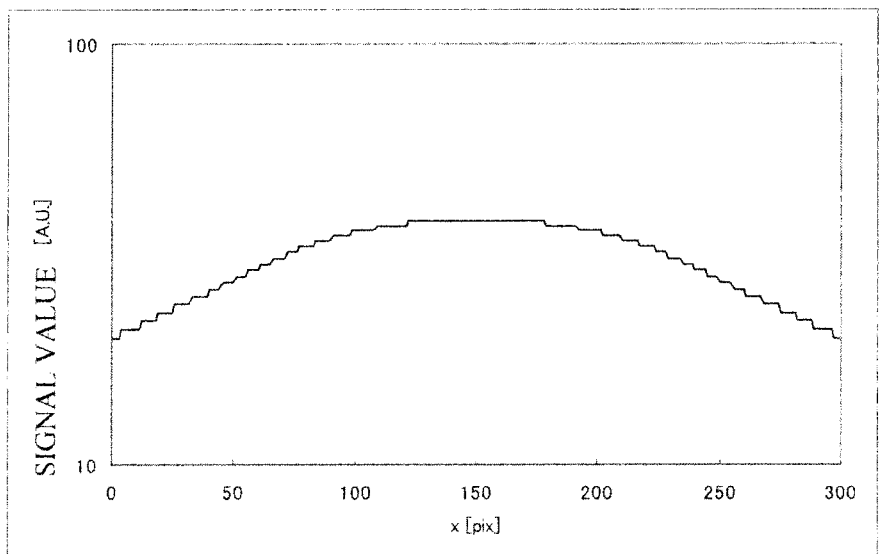

Thus, the following fact ensures accurate estimation of the secondary scattered X-rays S2 even when the subject data D2 is adopted. FIGS. 8 and 9 show estimates of scattered X-rays determined with Monte Carlo simulation. Each drawing has a horizontal axis indicating arrangement of the detecting elements. That is, in this simulation, scattered X-rays are estimated under assumption that 300 detecting elements are arranged in one row.

FIG. 8 shows a simulation result of obtaining estimates of the secondary scattered X-rays through selecting the distribution patterns F with use of direct X-rays and summing them up. FIG. 9 shows a simulation result of obtaining estimates of the secondary scattered X-rays through selecting the distribution patterns F with use of X-ray intensity outputted from each detecting element and summing them up. It is apparent that FIG. 8 has a profile extremely similar to FIG. 9. Thus, scattered X-rays may be estimated when X-ray intensity is merely determined that is outputted from each detecting element. Here, X-ray intensity outputted from each detecting element corresponds to X-ray intensity for the detecting element, respectively, in the subject data D2. Accordingly, the secondary scattered-ray estimating section 11 may estimate the secondary scattered X-rays S2 based on the subject data D2, thereby determining an estimate estS2.

Direct-Ray Attenuation-Rate Acquiring Step T4

Figure 10:
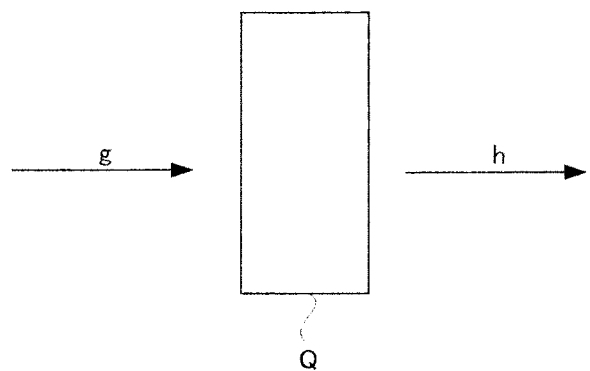
FIG. 10 is a schematic view showing a direct-ray attenuation-rate acquiring section according to the example.

The estimate estS2 of the secondary scattered X-rays is sent to the direct-ray attenuation-rate acquiring section 12. The direct-ray attenuation-rate acquiring section corresponds to the direct-ray attenuation-rate acquiring device in this invention. Description will be given of an attenuation rate of X-rays prior to description on operation of the direct-ray attenuation-rate acquiring section 12. As shown in FIG. 10, supposing that X-rays g enter into an object Q and X-rays h are emitted, an attenuation rate is h/g. In other words, an attenuation rate is an index of how X-rays readily transmit an object. Here in the X-ray apparatus 1, an attenuation rate is determined letting direct X-rays P1 (see Equation 1) emitted from the compensating filter 5 be X-rays g and direct X-rays P2 transmitting the subject be X-rays h. Here, a value of P2/P1 is an attenuation rate of direct rays (direct-ray attenuation rate A). By omitting scattered X-rays and determining the attenuation rate of only direct rays, a fluoroscopic X-ray image p of high contrast may be acquired. The direct-ray attenuation rate A may be given as follows from Equation 3:

$$A = (Gobj - S2 - w(S1))/P1 \tag{3}$$

Here, Gobj in Equation 3 is X-ray intensity represented by the subject data D2, and thus is measurable actually. The foregoing estimate estS2 is adopted for S2. Accordingly, direct-ray attenuation rate A may be determined through obtaining w(S1) and P1.

Now, description is given of how to determine w(S1). The number w(S1) is weakened primary scattered X-rays S1 that is generated due to transmitting of scattered X-rays generated with the compensating filter 5 through the subject. Here, an attenuation rate of the primary scattered X-rays S1 (primary scattered-ray attenuation rate) will be given as w (S1)/S1.

The primary scattered X-rays S1 are X-rays having slightly disturbed traveling directions and energy due to Compton scattering. Accordingly, it is proved by Monte Carlo simulation that the behavior of attenuating the primary scattered X-rays S1 is basically similar to that of attenuating direct X-rays. Then, it is assumed that the attenuation rate of the primary scattered X-rays S1 is equal to the direct-ray attenuation rate "A", which may be expressed by the following Equation:

$$w(S1)/S1 = A \tag{4}$$

W(S1) is eliminated from Equation 3 with use of Equation 4 to be the following:

$$A = (Gobj - S2 - A \cdot S1)/P1 \tag{5}$$

This is rearranged on A to be the following:

$$A = (Gobj - S2)/(P1 + S1) \tag{6}$$

Estimate estS2 may instead be used for the secondary scattered X-rays S2 in Equation 6. In addition, P1+S1 is exactly Gair from Equation 1. Accordingly, Equation 6 may be expressed as the following equation:

$$A = (Gobj - estS2)/Gair \tag{7}$$

The direct-ray attenuation-rate acquiring section 12 determines a direct-ray attenuation rate A for each detecting element from Gair (air data D1), Gobj (subject data D2), and estimate estS2 with use of relation in Equation 7. These are all values that may be measured and estimated. The direct-rays attenuation rate A thus obtained is sent to the fluoroscopic image generating section 13. Here, the fluoroscopic image generating section corresponds to the image generating section in this invention.

Image Generating Step T5

The fluoroscopic image generating section 13 generates a fluoroscopic X-ray image p having a fluoroscopy image of the subject M appearing therein by normalizing direct-rays attenuation rates A determined for every detecting element with appropriate value and arranging them two-dimensionally. Thus, acquisition of a fluoroscopic X-ray image with the X-ray apparatus 1 according to the example can be completed.

As noted above, this example includes the direct-ray attenuation-rate acquiring section 12 for acquiring an attenuation rate of direct X-rays P from a dose of direct X-rays P1 entering into the subject M and a dose of direct X-rays P2 emitted from the subject M. Determination of the direct-ray attenuation rate A may achieve acquisition of a fluoroscopic X-ray image p of an excellent contrast with no influence of scattered radiation S. On the other hand, the X-ray apparatus 1 in this example includes the compensating filter 5 for controlling a dose of radiation that has some difficulty in acquiring the direct-ray attenuation rate A. The configuration of the example solves this difficulty as follows.

Primary scattered-radiation S1 generated through the compensating filter 5 attenuates in the subject M and enters into the FPD 4. The way of determining the attenuated primary scattered-radiation w(S1) becomes important upon acquisition of a direct-ray attenuation rate A. That is, in this example, a direct-ray attenuation rate A is acquired on an assumption that a primary scattered-ray attenuation rate is equal to the direct-ray attenuation rate A, the primary scattered-ray attenuation rate being as a rate of decreasing primary scattered radiation S1 that passes through (transmits) the subject M. Here, primary scattered-radiation S1 is X-rays with a traveling direction and energy thereof being slightly changed due to Compton scattering. In other words, the behavior of attenuating the primary scattered-radiation in the subject M may be considered similar to that of attenuating direct X-rays P. As noted above, it is assumed that the primary scattered-ray attenuation rate is equal to the direct-ray attenuation rate A. Accordingly, an amount of direct X-rays transmitting through the subject M may be determined without performing complicated calculations conventionally. Therefore, the X-ray apparatus 1 may be provided that allows more simple acquisition of a fluoroscopic X-ray image. That is, the direct-ray attenuation rate A may be determined through a simple calculation as Equation 7 as in the above example.

With the configuration above, the compensating filter 5 may be modified optionally according to purposes of imaging. In addition, even when the compensating filer 5 is replaced or changed in shape, once performance of air radiography may achieve accurate acquisition of the direct-ray attenuation rate A.

Figure 11:
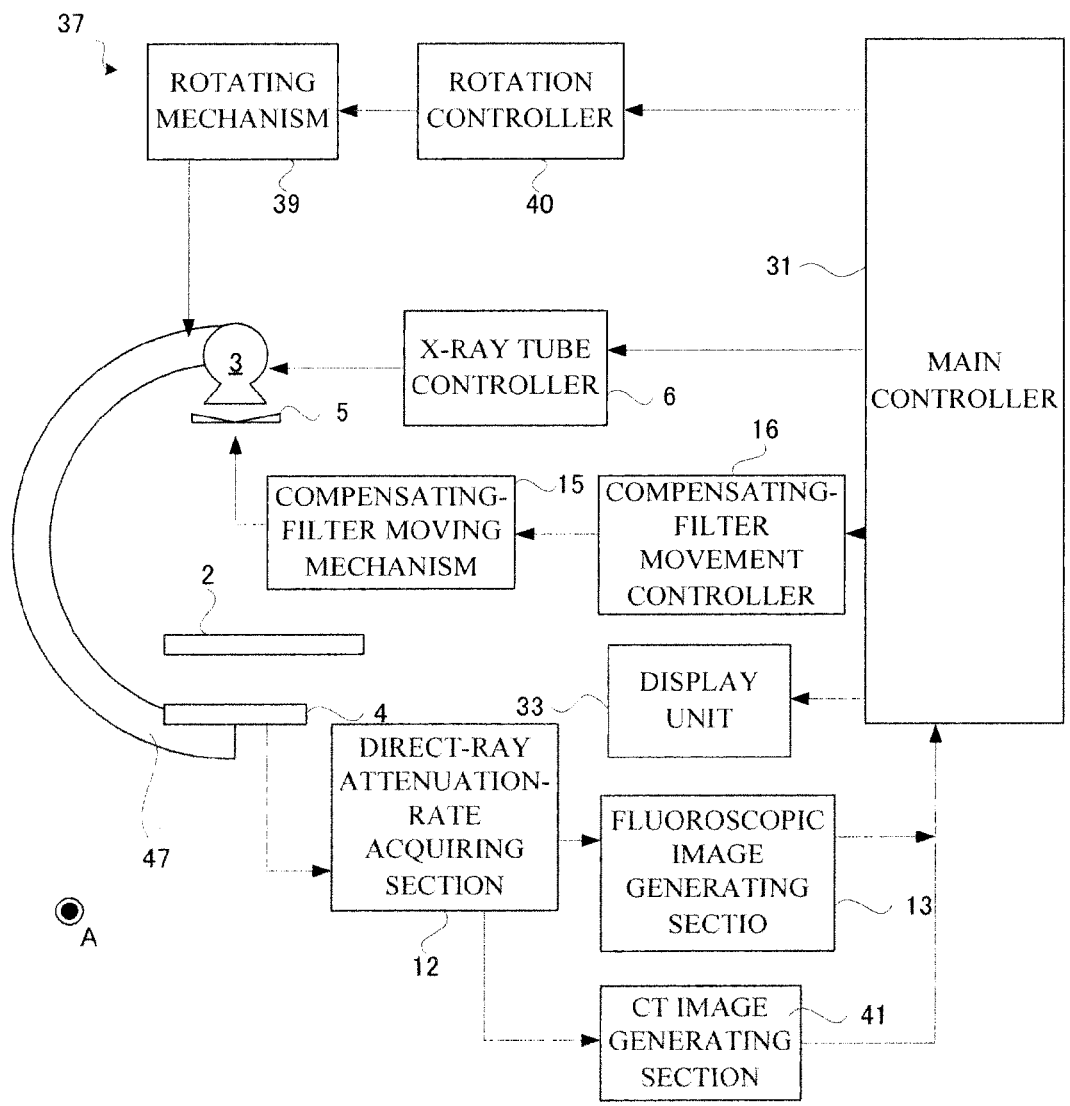
FIG. 11 is a functional block diagram showing X-ray apparatus according to another example.
Figure 12A:
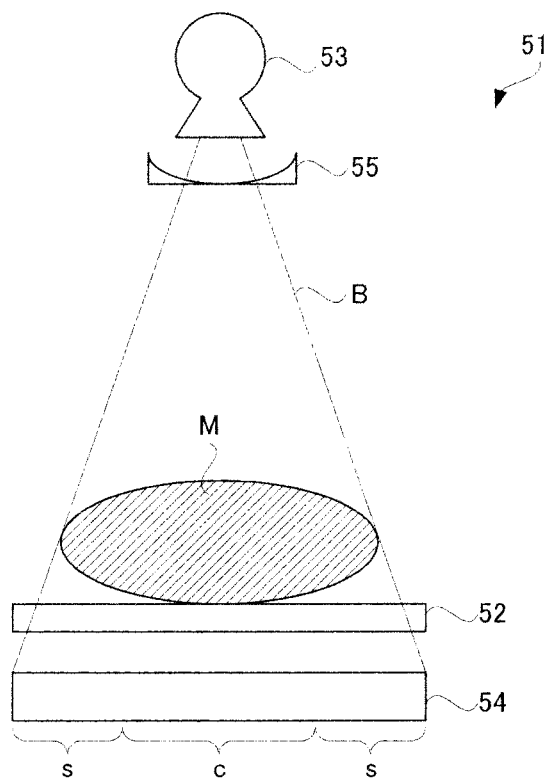
FIGS. 12 and 13 are plan views each showing the conventional radiographic apparatus.
Figure 12B:
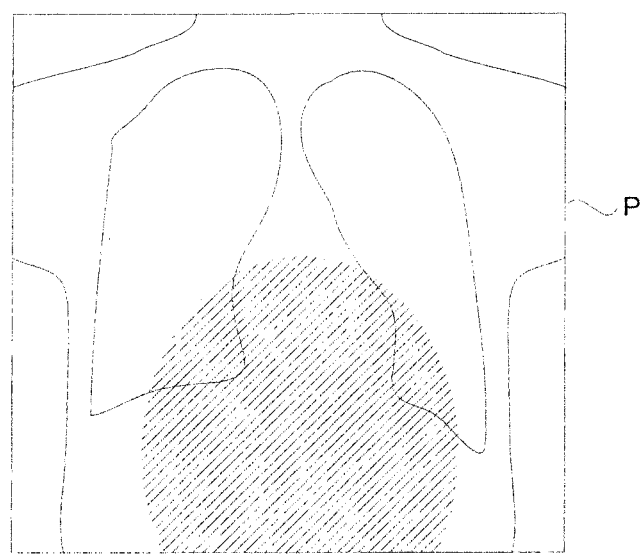
Figure 13:
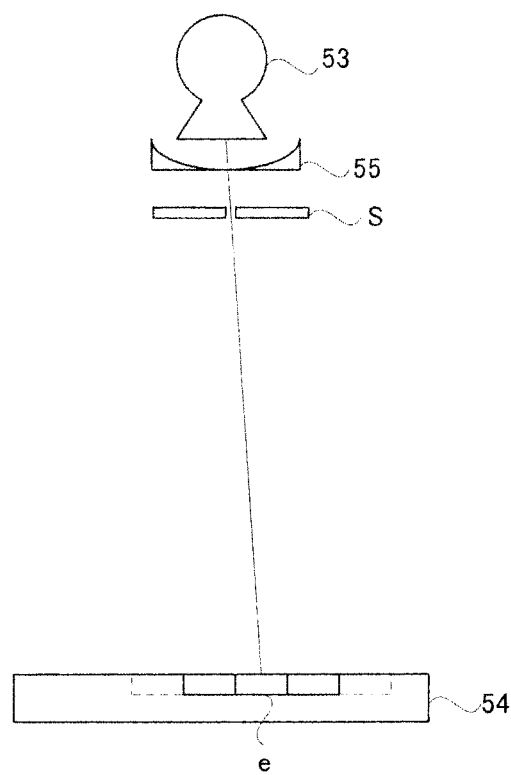

Next, description will be given of X-ray apparatus according to another example. Tomographic X-ray apparatus 37 according to this examples additionally includes each section as shown in FIG. 11 in addition to each section as shown in FIG. 1 in the above example.

The tomographic X-ray apparatus 37 includes an X-ray tube 3 for irradiating a subject with X-rays, an FPD (flat panel detector) 4, and a supporting portion 47 for supporting the X-ray tube 3 and the FPD 4. The supporting portion 47 has a C-shape, and freely rotates about a body axis A of the subject M. A rotating mechanism 39 formed of a power generating device such as a motor and a power transmission device such as a gear performs rotation of the supporting portion 47. A rotation controller 40 controls the rotating mechanism 39. The supporting portion corresponds to the supporting device herein. The rotating mechanism corresponds to the rotating device herein. The rotation controller corresponds to the rotation control device herein.

The CT image generating section 41 generates an X-ray sectional image of the subject M in accordance with X-ray detection data outputted from the direct-ray attenuation-rate acquiring section 12 in FIG. 1. The CT image generating section corresponds to the image generating device herein. Of course, the subject image described in the example above may be generated also in this example by sending X-ray detection data from the direct-ray attenuation-rate acquiring section 12 to the fluoroscopic image generating section 13.

The CPU 31 performs execution of various programs to achieve the rotation controller 40 and the CT image generating section 41, in addition to each section according to the above example. The above sections may each be individually operated by a controller that performs their functions.

Now, description is given of a method for acquiring a fluoroscopic X-ray image. The X-ray tube 3 and the FPD 4 rotate about the z-axis while a relative position therebetween is maintained. Here, the X-ray tube 3 intermittently irradiates the subject M with X-rays, and the direct-ray attenuation-rate acquiring section 12 acquires direct-ray attenuation rate A for every irradiation. The positional information on the detecting element has been sent from the FPD 4 to the direct-ray attenuation-rate acquiring section 12. The direct-ray attenuation-rate acquiring section 12 may discriminate a position in the FPD 4 where the direct-ray attenuation rate A is derived. Moreover, the direct-ray attenuation-rate acquiring section 12 acquires, from the rotation controller 40, inclination information representing inclination angles of the X-ray tube 3 and the FPD 4 when they rotate. The direct-ray attenuation rate A is correlated with positional information and inclination information in the FPD 4 by the direct-ray attenuation-rate acquiring section 12, and is sent to the CT image generating section 41. The CT image generating section 41 constructs a group of data on the direct-ray attenuation rates A into a signal sectional image with use of an existing back projection method.

Moreover, air data and subject data may be acquired upon determining the direct-ray attenuation rate A. At this time, the compensating-filter movement controller 16 changes relative position of parts 5a of the compensating filter 5 (see FIG. 3) along with rotation of the X-ray tube 3. A thickness of X-ray beams emitted from the X-ray tube 3 when passing through the subject and a region where the subject interrupts the X-ray beams continuously is each changed in accordance with variations in inclination angle of the X-ray tube 3. Accordingly, the relative position of the parts 5a is changed. The compensating filter movement controller 16 changes the relative position of the parts 5a in a manner similar to that upon acquisition of subject data.

According to this example, the compensating filter 5 varies in shape in accordance with variations in inclination angle of the X-ray tube 3. Accordingly, for acquiring a sectional image with the conventional configuration, scattered should be estimated under a state where the subject is not placed on the top board 2. Since the compensating filter 5 varies in shape for every irradiation of the X-ray tube 3 with X-rays, estimation of direct X-rays should be made for every X-ray irradiation. On the other hand, with the configuration of this example, such calculation is not needed. Accordingly, the tomographic X-ray apparatus 37 may be provided with significantly improved calculation efficiency.

As mentioned above, the configuration of this example may achieve acquisition of a sectional image of the subject M. That is, the direct-ray attenuation rate A may be acquired while the supporting portion 47 rotates. And the CT image generating section 41 generates a sectional image based on this rate. Accordingly, the tomographic X-ray apparatus 37 may be provided that allows acquisition of a sectional image with high contrast.

This invention is not limited to each of the foregoing examples, but may be modified as follows.

(1) Each foregoing example discusses a medical apparatus. This invention is applicable also to apparatus for industrial use and for the nuclear field.

(2) X-rays used in each foregoing example are an example of radiation in this invention. Therefore, this invention may be adapted also for radiation other than X-rays (e.g. gamma-rays).

(3) In each of the foregoing examples, the air-data acquiring step T1 is performed, and subsequently the subject-data acquiring step T2 is performed. Alternatively, this may be performed in a reverse order.

As described above, this invention is suitable for medical fields.

The invention claimed is:

1. A radiographic apparatus comprising:
a radiation source emitting radiation;
a compensating filter provided on the radiation source controlling a dose of the radiation;
a detecting device detecting radiation transmitting through the compensating filter to output detection data;
an air-data storage device storing air data as detection data that is acquired under a state where a subject is not placed between the radiation source and the detecting device;
a subject-data storage device storing subject data as detection data that is acquired under a state where the subject is placed between the radiation source and the detecting device;
a secondary scattered-ray estimating device estimating a dose of secondary scattered radiation that enters into the detecting device based on the subject data, the secondary scattered radiation being scattered radiation generated with the subject
a direct-ray attenuation-rate acquiring device acquiring a direct-ray attenuation rate based on the air data, the subject data, and an estimated dose of the secondary scattered radiation, the direct-ray attenuation rate being a rate of a dose of direct radiation from the compensating filter before transmitting through the subject to a dose of the direct radiation after transmitting through the subject; and
an image generating device generating an image having a subject image appearing therein in accordance with the direct-ray attenuation rate,
wherein the direct-ray attenuation-rate acquiring device acquires the direct-ray attenuation rate on an assumption that a primary scattered-ray attenuation rate is equal to the direct-ray attenuation rate, the primary scattered-ray attenuation rate representing a rate of a dose of primary scattered radiation generated by the compensating filter before transmitting through the subject to a dose of the primary scattered radiation after transmitting through the subject, the primary scattered radiation being scattered radiation generated with the compensating filter.

2. The radiographic apparatus according to claim 1, wherein
the direct-ray attenuation-rate acquiring device acquires a direct-ray attenuation rate using the following equation:

$$Rd=(Is-Ie)/Ia,$$

where $Rd$ denotes the direct-ray attenuation-rate, $Is$ denotes a radiation intensity from subject data, $Ie$ denotes an estimated secondary scattered-radiation intensity, and $Ia$ denotes a radiation intensity from the air data.

3. The radiographic apparatus according to claim 1, wherein
the compensating filter is removable from the radiation source.

4. The radiographic apparatus according to claim 1, wherein
the compensating filter comprises a plurality of parts variable in relative position therebetween, and further comprises:
a compensating filter moving device moving the parts; and
a compensating filter control device controlling the compensating filter moving device.

5. The radiographic apparatus according to claim 1, further comprising:
a supporting portion supporting the radiation source and the detecting device;
a rotating device rotating the supporting portion; and
a rotation control device controlling the rotating device,
wherein the image generating device generates a sectional image in accordance with a series of direct-ray attenuation rates acquired while the supporting portion is rotated.

6. A method of obtaining an image with use of detection data acquired by radiographic apparatus having a radiation source for emitting radiation, a compensating filter provided on the radiation source for controlling a dose of radiation, and a detecting device for detecting radiation transmitting through the compensating filter to output detection data, comprising:
an air-data acquiring step acquiring air data as detection data that is acquired under a state where a subject is not placed between the radiation source and the detecting device;
a subject-data acquiring step acquiring subject data as detection data that is acquired under a state where the subject is placed between the radiation source and the detecting device;
a secondary scattered-ray estimating step estimating a dose of secondary scattered radiation that enters into the detecting device based on the subject data, the secondary scattered radiation being scattered radiation generated with the subject;
a direct-ray attenuation-rate acquiring step acquiring a direct-ray attenuation rate based on the air data, the subject data, and an estimated dose of the secondary scattered radiation, the direct-ray attenuation rate being a rate of a dose of direct radiation from the compensating filter before transmitting through the subject to a dose of the direct radiation after transmitting through the subject; and
an image generating step generating an image having a subject image appearing therein in accordance with the direct-ray attenuation rate,
wherein in the direct-ray attenuation-rate acquiring step, the direct-ray attenuation rate is acquired on an assumption that a primary scattered-ray attenuation rate is equal to the direct-ray attenuation rate, the primary scattered-ray attenuation rate representing a rate of a dose of primary scattered radiation generated by the compensating filter before transmitting through the subject to a dose of the primary scattered radiation after transmitting through the subject, the primary scattered radiation being scattered radiation generated with the compensating filter.

7. The method of obtaining an image according to claim 6, wherein
in the direct-ray attenuation-rate acquiring step, a direct-ray attenuation rate is acquired using the following equation:

$$Rd=(Is-Ie)/Ia,$$

where Rd denotes the direct-ray attenuation-rate, Is denotes a radiation intensity from subject data, Ie denotes an estimated secondary scattered-radiation intensity, and Ia denotes a radiation intensity from the air data.

* * * * *